US00PP23629P3

(12) United States Plant Patent
Olesen

(10) Patent No.: US PP23,629 P3
(45) Date of Patent: May 28, 2013

(54) CLIMBING ROSE PLANT NAMED 'POULCY015'

(50) Latin Name: *Rosa hybrida*
Varietal Denomination: Poulcy015

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 13/317,239

(22) Filed: Oct. 13, 2011

(65) Prior Publication Data

US 2013/0097743 P1 Apr. 18, 2013

(51) Int. Cl.
*A01H 5/00* (2006.01)

(52) U.S. Cl.
USPC ..... Plt./115

(58) Field of Classification Search
USPC ..... Plt./115
See application file for complete search history.

*Primary Examiner* — Kent L Bell

(57) ABSTRACT

A new garden rose plant of the climbing class which has abundant, red flowers and attractive foliage. This new and distinct variety has shown to be uniform and stable in the resulting generations from asexual propagation.

3 Drawing Sheets

Botanical designation: *Rosa hybrida.*
Variety denomination: 'Poulcy015'.

SUMMARY OF THE INVENTION

The present invention constitutes a new and distinct variety of garden rose plant which originated from a controlled crossing between the female seed parent, an unnamed seedling, and the male pollen parent, an unnamed seedling.

The two parents were crossed during the summer of 1998 and the resulting seeds were planted in a controlled environment in Fredensborg, Denmark. The new variety, named 'Poulcy015', originated as a single seedling from the stated cross.

The new variety may be distinguished from its female seed parent by flower size. The female seed parent has large very double flowers while the new variety has smaller flowers with 20 petals.

The new variety may be distinguished from its male pollen parent by growth habit. The male parent plant is compact and bushy, while the new variety has an arching habit.

The objective of the hybridization of this rose variety was to create a new and distinct variety for container and garden use with unique qualities, such as:

1. Uniform and abundant red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy015' from all other varieties of which we are aware.

As part of the rose development program, Mogens N. Olesen germinated the seeds from the aforementioned hybridization during winter of 1998 and conducted evaluations on the resulting seedlings in a controlled environment in Fredensborg, Denmark. 'Poulcy015' was selected in the spring of 1999 by the inventor as a single plant from the progeny of the aforementioned hybridization.

Asexual reproduction of 'Poulcy015' by traditional budding and rooted cuttings was first done by Mogens N. Olesen in the nursery in Fredensborg, Denmark in July, 1999. This initial and other subsequent asexual propagations conducted in controlled environments have demonstrated that the characteristics of 'Poulcy015' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy015'. Specifically illustrated in the drawing are.

DETAILED DESCRIPTION OF THE VARIETY

Figure 1:
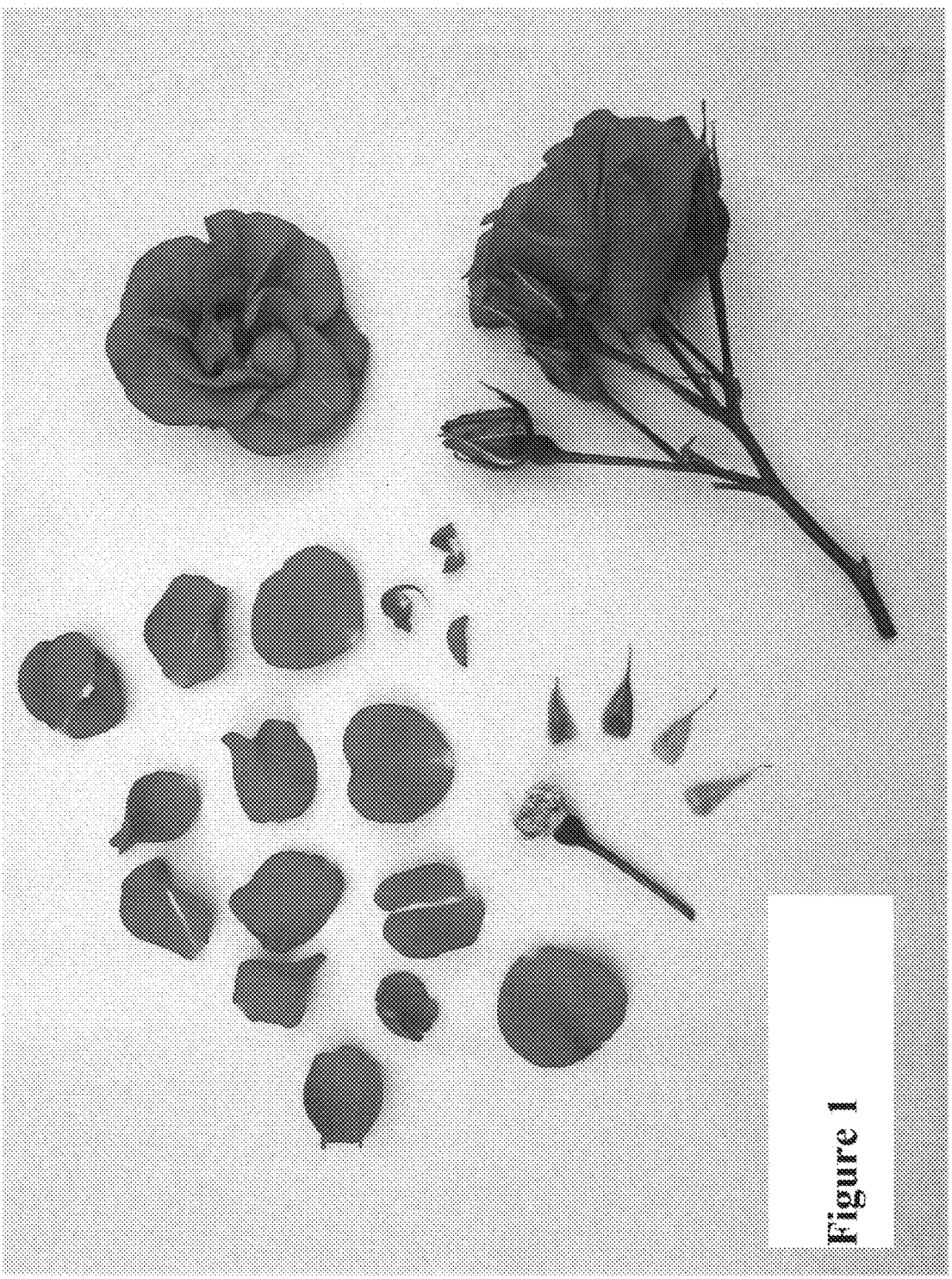
FIG. 1; Open flower, stem showing open flower, branching, and the attachment of buds, peduncles and pedicels, petals detached, flower parts, and sepals.
Figure 2:
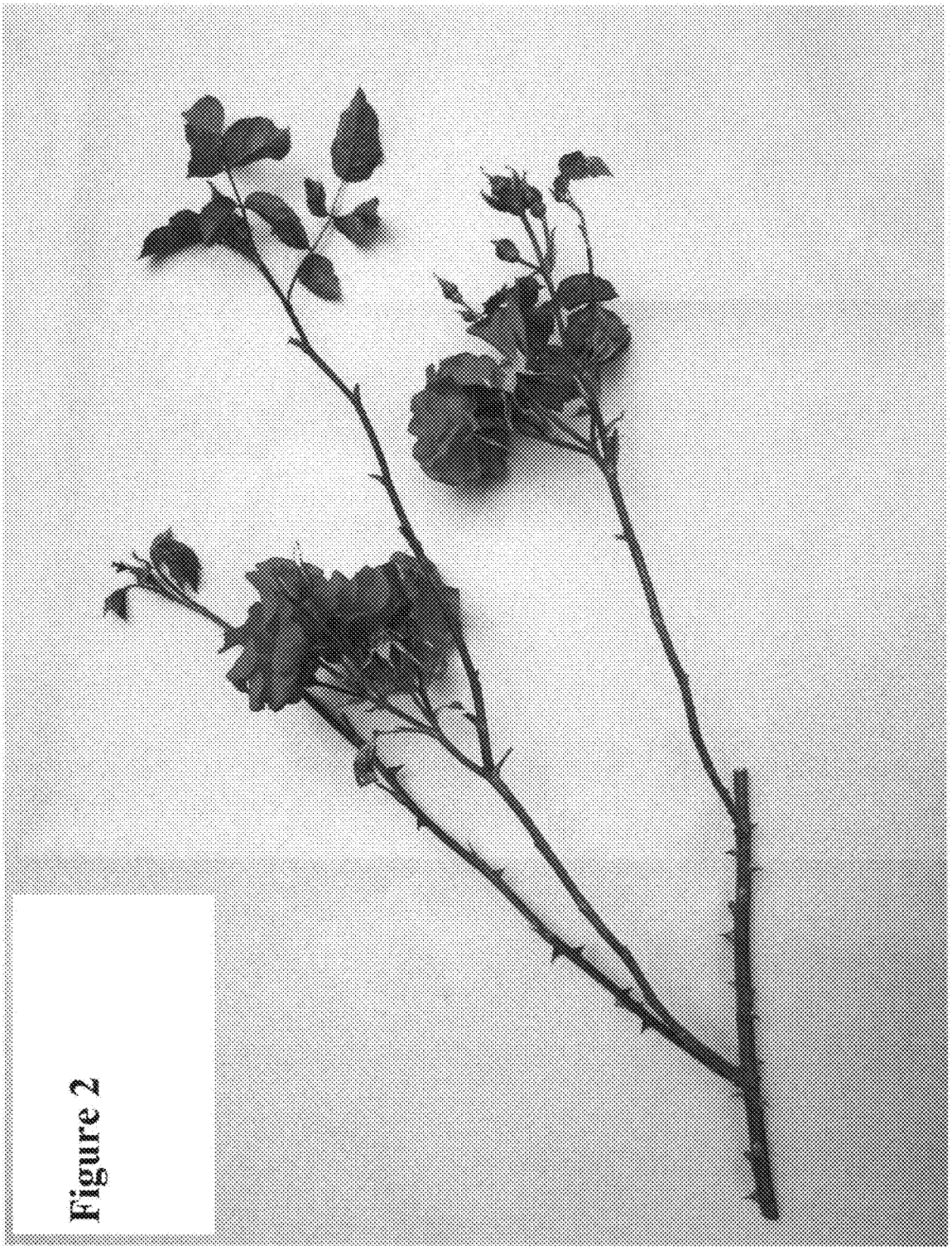
FIG. 2; Flowering branches attached to main stem.
Figure 3:
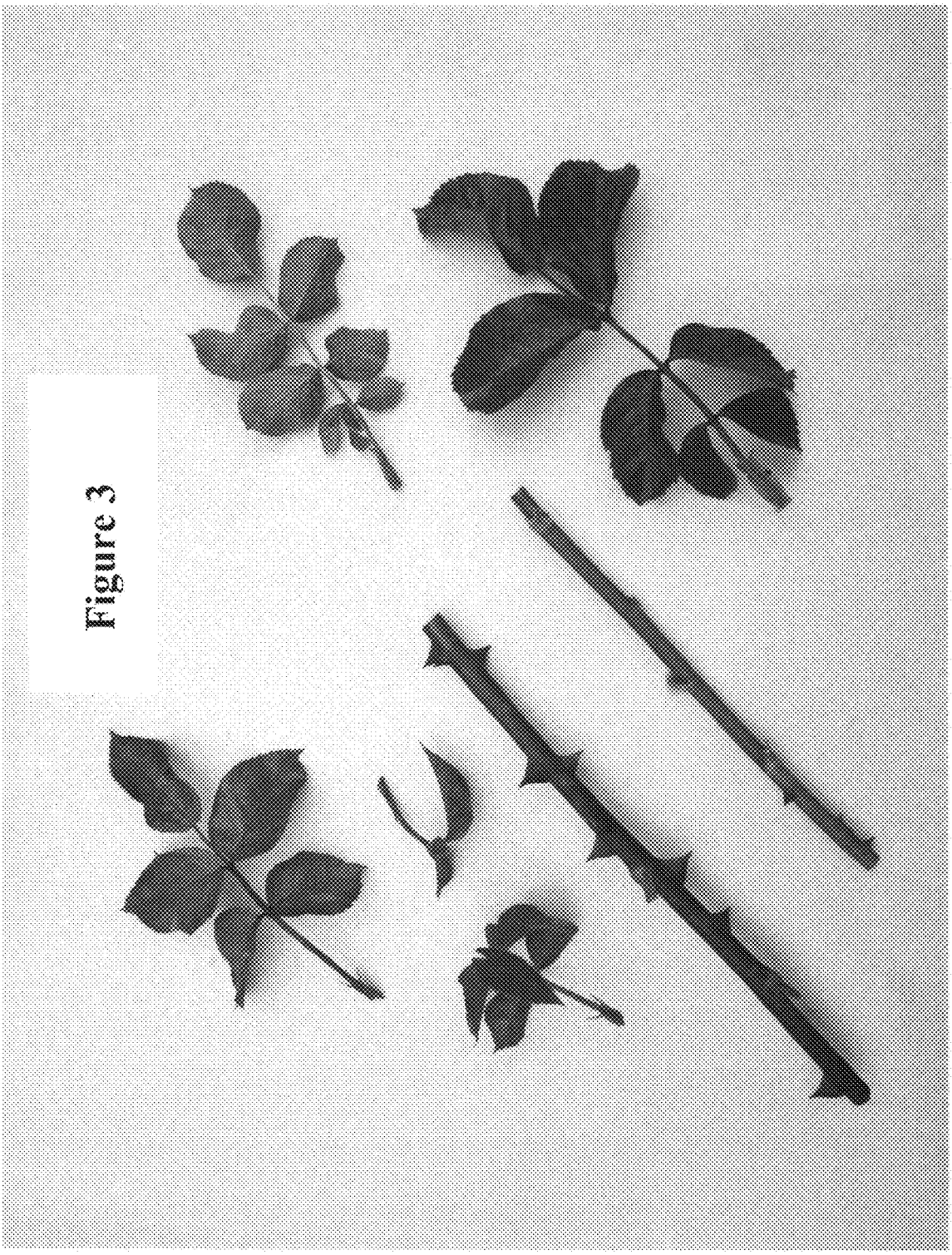
FIG. 3; Leaves and stems.

The following is a description of 'Poulcy015', as observed in its growth in a field nursery in Benton County Oreg. Observed plants are 3 years of age, grown on *Rosa multiflora* understock. Color references are made using The Royal Horticultural Society (London, England) Colour Chart, 2001, except where common terms of color are used.

For a comparison, several physical characteristics of the rose variety 'Poulnorm', U.S. Plant Pat. No. 12,522 are compared to 'Poulcy015' in Chart 1.

CHART 1

| | 'Poulcy015' | 'Poulnorm' |
|---|---|---|
| Petal Count | 20 | 45 to 50 |
| Flower Diameter | 75 to 90 mm | 100 mm |

CHART 1-continued

| | 'Poulcy015' | 'Poulnorm' |
|---|---|---|
| After opening petal color, upper | Red Group 45B. | Red Group 34A |

FLOWER AND FLOWER BUD

Blooming habit: Stages of continuous periods of bloom.

Flower bud:

*Size*.—Upon opening, 25 mm in length from base of receptacle to end of bud. Bud diameter is 11 mm.

*Bud form*.—Urceolate.

*Bud color*.—As sepals unfold, petals are Red Group 45A and 46A.

*Sepal inner surface*.—Color: Yellow-Green Group 146D. Surface: Smooth with weak pubescence.

*Sepal outer surface*.—Color: Yellow-Green Group 144A. Strong anthocyanic pigments the color of Greyed-Purple Group 183A observed. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—32 mm long by 9 mm wide.

*Receptacle*.—Texture: Smooth. Shape: Elliptical. Size: 11 mm tall by 9 mm wide. Color: Yellow-Green Group 144A. Strong anthocyanic pigments the color of Greyed-Purple Group 183A observed.

*Peduncle*.—Length: 30 to 70 cm in length. Diameter: 3 to 5 mm. Color: Yellow-Green Group 144A with strong anthocyanic intonations the color of Greyed-Purple Group 183A. Texture: Smooth.

*Pedicel*.—Surface: Smooth. Length: 40 to 45 mm. Diameter: 2 to 3 mm. Color: Varying from Yellow-Green Group N144A to 144A. Strong anthocyanic intonations the color of Greyed-Purple Group 183A. Strength: Moderate.

Flower bud development: Flower buds are borne in clusters, resembling a panicle. Each flowering branch contains 9 to 11 flower buds. Reduced apical dominance in flower habit causes flower buds develop in stages from the base of the plant to the upper branches.

Flower bloom:

*Fragrance*.—Moderate old rose scent.

*Duration*.—The blooms have a duration on the plant of approximately 10 days. Petals fall cleanly away from plant after flowers have fully matured.

*Size*.—Flower diameter is 75 to 90 mm when open. Flower depth is 30 mm.

*Flower shape*.—General shape is an open cup.

*Shape of flower, side view*.—The upper portion is flat, while the lower portion is concave.

Petalage: Under normal conditions, flowers have 20 petals total, 3 to 5 of which are petaloids.

Petal color upon opening and after opening:

*Outer petals*.—Upper surface: Red Group 45B. Lower surface: Red Group 53B.

*Inner petals*.—Upper surface: Red Group 45B. Occasionally, petals are vertically splashed with Yellow Group 4D at the middle. Lower surface: Red Group 53B. Occasionally, petals are vertically splashed with Yellow Group 4D at the middle.

*Basal petal spots*.—Upper surface: Yellow-Green Group 8A. Lower surface: Yellow-Green Group 8A.

General tonality: On open flower Red Group 45B. Color remains for the duration of the flower.

*Petal reflex*.—Weak.

*Margin*.—Entire and uniform. Medium strong undulations of margin observed.

*Shape*.—Generally broad elliptic. Apex shape: Rounded. Base shape: Acute.

*Size*.—Outer petals are 35 mm long by 40 mm wide. Inner petals are 30 mm long by 30 mm wide.

*Texture*.—Smooth.

*Thickness*.—Average.

Petaloids:

*Quantity*.—3 to 5.

*Shape*.—Irregular. Apex is rounded. Base is acute.

*Color*.—Upper surface is Red Group 45B. Occasionally, petals are vertically splashed with Yellow Group 4D at the middle. Lower surface is Red Group 53B. Occasionally, petals are vertically splashed with Yellow Group 4D at the middle.

*Size*.—30 mm (l)×30 mm (w).

Reproductive organs:

*Pollen*.—None observed.

*Anthers*.—Size: 2 mm in length. Color: Yellow-Green Group 11B. Quantity: 75 on average.

*Filaments*.—Color: At the base, Yellow Group 5B. Upper portion is Red Group 42B. Length: 10 mm.

*Pistils*.—Length: 5 mm. Quantity: 65 on average.

*Stigmas*.—Inferior in location relative to the length of the filaments and the height of the anthers. Color: Greyed-Yellow Group 161D.

*Styles*.—Color: Greyed-Yellow Group 161D.

*Hips*.—None observed.

PLANT

Plant growth: Arching. When grown as a budded field grown plant on *Rosa multiflora* understock, the average height of the plant is 100 cm and the average width is 115 cm.

Stems:

*Color*.—Juvenile growth: Greyed-Red Group 178A. Mature growth: Yellow-Green Group 144A.

*Length*.—Canes are 25 to 40 cm from the base of the plant to the flowering portion.

*Diameter*.—6 mm.

*Internodes*.—On mature canes, there is an average distance of 35 mm between nodes.

*Surface texture*.—Young wood: Smooth. Older wood: Smooth.

Prickles:

*Incidence*.—2 to 5 prickles per 10 cm of stem.

*Size*.—Average length of prickles on mature stems is 10 mm.

*Shape*.—Concave.

*Color*.—Juvenile prickles: Greyed-Purple Group 187B. Mature prickles: Greyed-Red Group 182A.

Plant foliage: Normal number of leaflets per leaf in middle of the stem: 7 leaflets.

*Compound leaf*.—160 mm (l)×100 (w).

*Quantity*.—3 leaves per 10 cm of stem on average.

*Color of mature foliage*.—Upper side: Yellow-Green Group 146A. Lower side: Yellow-Green Group 146B.

*Color of juvenile foliage*.—Upper side: Yellow-Green Group 146C. Lower side: Yellow-Green Group 146C. Anthocyanin: Greyed-Orange Group 175A and Greyed-Purple Group 183A at the margins.

Plant leaves and leaflets:

*Stipules*.—Size: 20 to 25 mm in length. Quantity: 2 per compound leaf. Shape: Linear, slightly broad based with outward extending apices. Margins: Finely serrated with few stipitate glands. Color: Yellow-Green Group 144A.

*Petiole*.—Length: 40 mm on average. Diameter: 2 mm.

*Upper surface*.—Color: Yellow-Green Group N144A. Anthocyanin the color of Greyed-Orange Group 175B.

*Lower surface*.—Color: Yellow-Green Group 144B. Observations: Smooth.

*Rachis*.—Length: 70 mm on average. Upper surface: Greyed-Orange Group 176A.

*Lower surface*.—Color: Yellow-Green Group 144B. Observations: Smooth.

*Leaflet*.—Margin: Doubly serrated. Size: The terminal leaflet on normal leaves is 50 to 60 mm in length by 45 to 50 mm wide. Shape: Generally ovate. Base: Rounded. Apex: Mucronate. Texture: Smooth. Thickness: Above average. Arrangement: Odd pinnate. Venation: Reticulate. Glossiness: Moderately glossy.

Disease resistance: Above average resistance to powdery and downy mildew, rust, black spot, and Botrytis under normal growing conditions in Benton County, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the climbing rose class named 'Poulcy015', substantially as illustrated and described herein, due to its abundant red flowers, disease resistance, and extended period of bloom.

* * * * *